United States Patent
Bordignon et al.

(10) Patent No.: US 9,353,823 B2
(45) Date of Patent: May 31, 2016

(54) DEVICE AND METHOD FOR CHECKING THE STATE OF CHARGE OF A GAS SPRING

(71) Applicant: BORDIGNON SILVANO S.R.L.

(72) Inventors: Alberto Bordignon, Rosa (IT); Simone Bordignon, Rossano Veneto (IT)

(73) Assignee: BORDIGNON SILVANO S.R.L., Rossano Veneto (IT)

( * ) Notice: Subject to any disclaimer, the term of this patent is extended or adjusted under 35 U.S.C. 154(b) by 213 days.

(21) Appl. No.: 14/242,305

(22) Filed: Apr. 1, 2014

(65) Prior Publication Data

US 2015/0027219 A1    Jan. 29, 2015

(30) Foreign Application Priority Data

Jul. 23, 2013    (EP) ..................... 13425104

(51) Int. Cl.
*G01L 1/04* (2006.01)
*F16F 9/43* (2006.01)
*F16F 9/32* (2006.01)

(52) U.S. Cl.
CPC ................. *F16F 9/43* (2013.01); *F16F 9/3264* (2013.01); *G01N 2203/0288* (2013.01); *G01N 2203/0292* (2013.01)

(58) Field of Classification Search
None
See application file for complete search history.

(56) References Cited

U.S. PATENT DOCUMENTS

| | | | |
|---|---|---|---|
| 2,948,256 A | 8/1960 | Tapp | |
| 3,106,993 A | 10/1963 | May | |
| 3,421,369 A | 1/1969 | Freehauf | |
| 5,172,892 A * | 12/1992 | Wallis | F16F 9/0209 267/119 |
| 5,197,718 A * | 3/1993 | Wallis | F16F 9/0218 137/68.23 |
| 5,318,281 A * | 6/1994 | Wallis | F16F 9/0209 267/119 |
| 5,469,978 A | 11/1995 | Bankos et al. | |
| 5,975,507 A * | 11/1999 | Cotter | F16F 9/43 267/64.11 |
| 2002/0152790 A1* | 10/2002 | Kelm | B21D 24/02 72/343 |
| 2004/0100006 A1* | 5/2004 | Kawahara | F16F 9/0218 267/118 |
| 2006/0231991 A1* | 10/2006 | Chun | F16F 9/0218 267/119 |
| 2011/0180360 A1 | 7/2011 | Martin et al. | |

FOREIGN PATENT DOCUMENTS

| | | | | |
|---|---|---|---|---|
| GB | 2285670 A * | 7/1995 | ............ | F16F 9/0245 |
| KR | 20110070111 A * | 6/2011 | | |

* cited by examiner

*Primary Examiner* — Andre Allen
(74) *Attorney, Agent, or Firm* — Pearne & Gordon LLP

(57) ABSTRACT

A device (1) for checking the state of charge of a gas spring (100), comprises: a supporting structure (2) equipped with connecting means (3) adapted to be reversibly connected to a gas spring (100); a plunger (4) slidably received, at least partly, in the supporting structure and having a first end (4*b*) adapted to interact, in conditions of use, with a charging valve of a gas spring, the plunger having a second end which has an abutment surface (4*d*); pushing means (6) operating on the abutment surface (4*d*) of the plunger (4) to apply a measured thrust on the plunger (4) such as to induce the displacement thereof; a position indicator (5) operatively associated with the plunger (4) and configured to represent the position of the plunger relative to a reference element (7). Also described is a method for checking the state of charge of a gas spring (100).

13 Claims, 5 Drawing Sheets

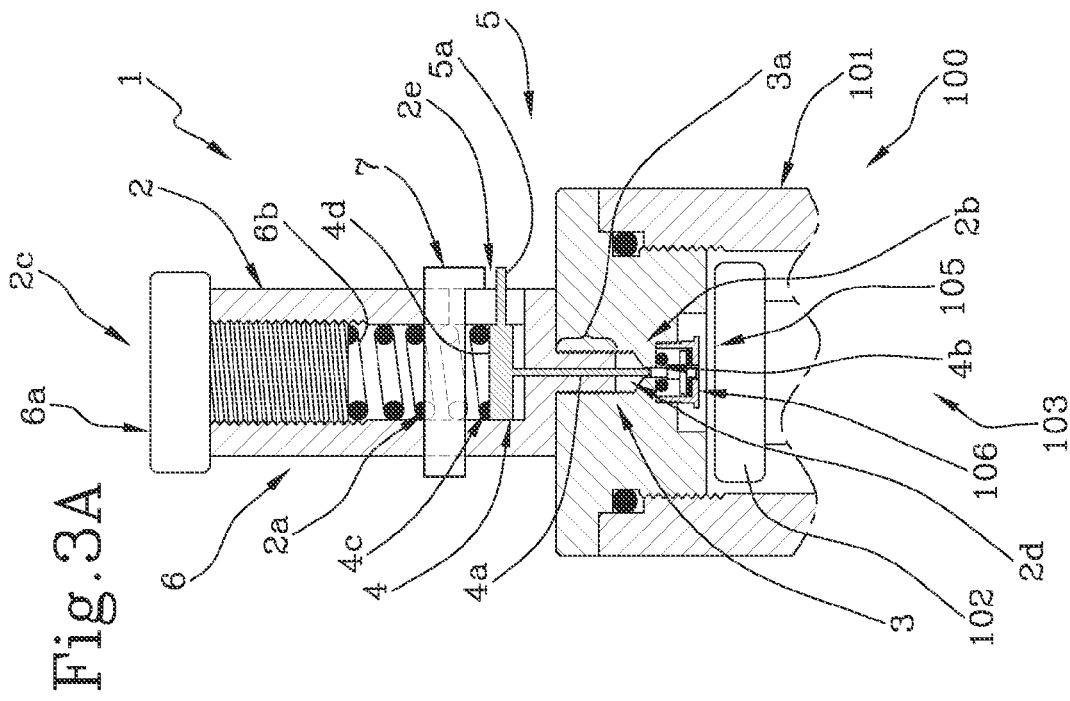
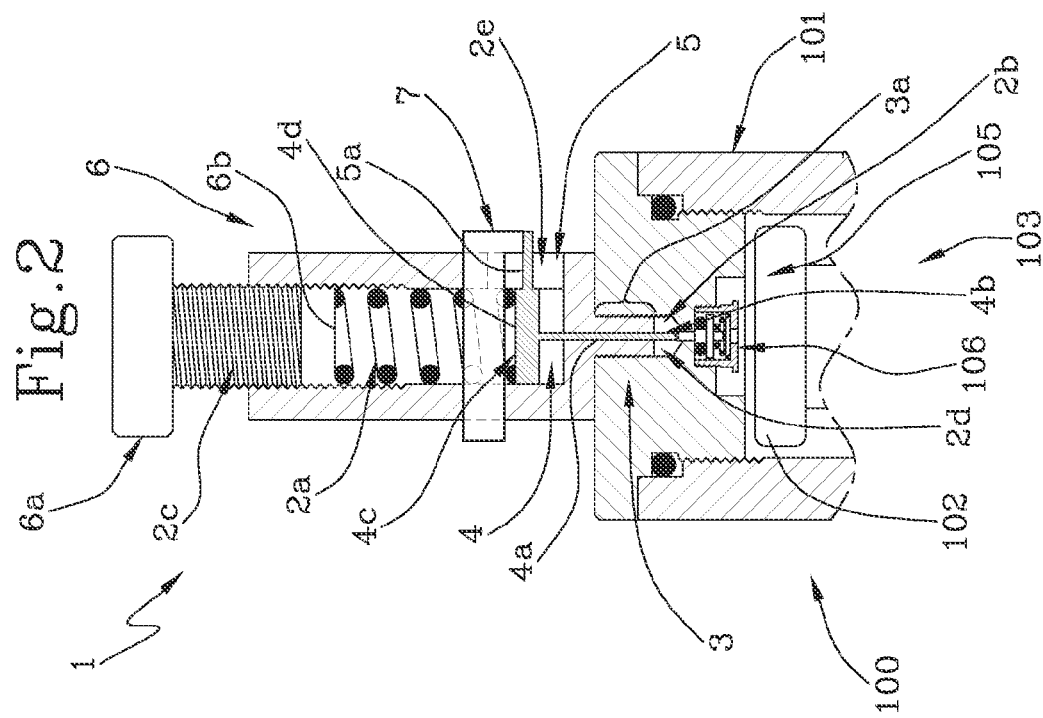

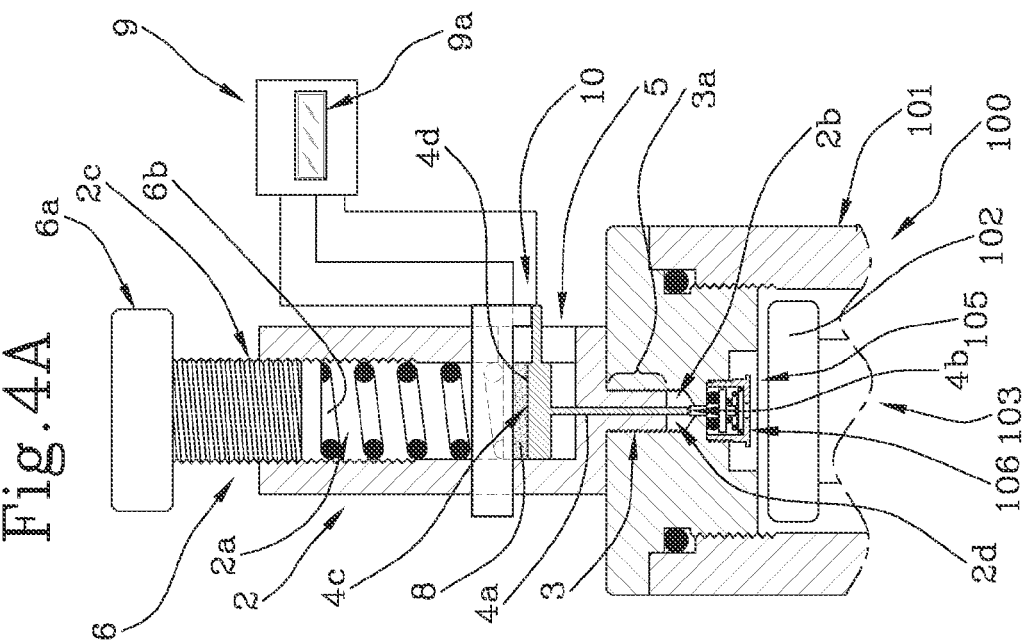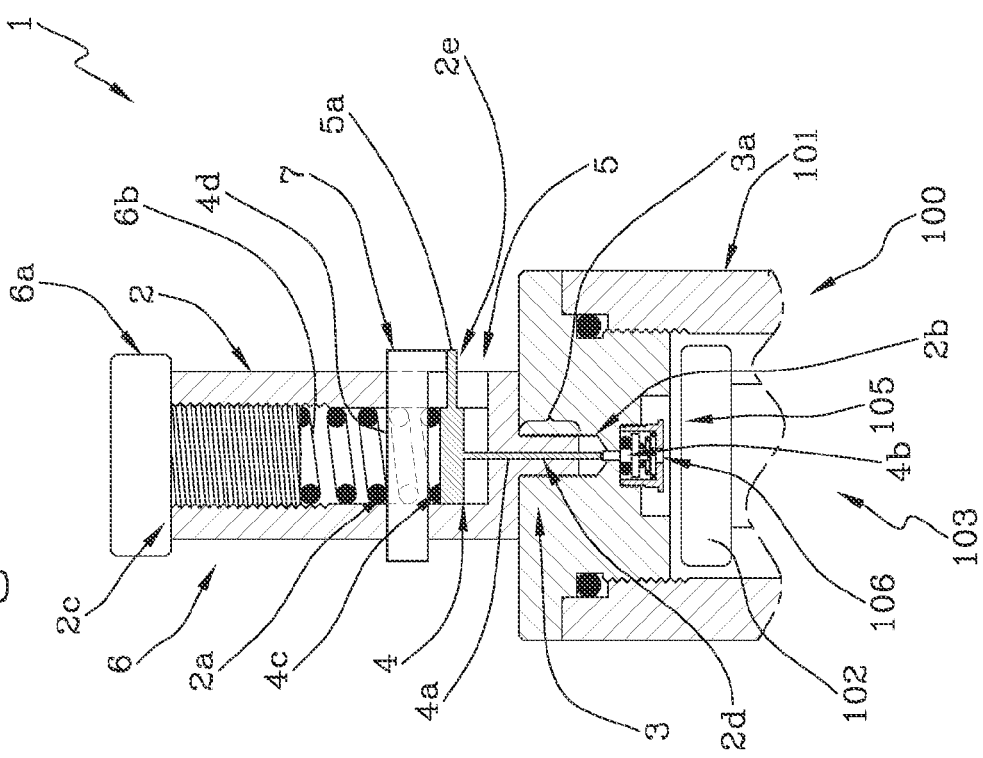

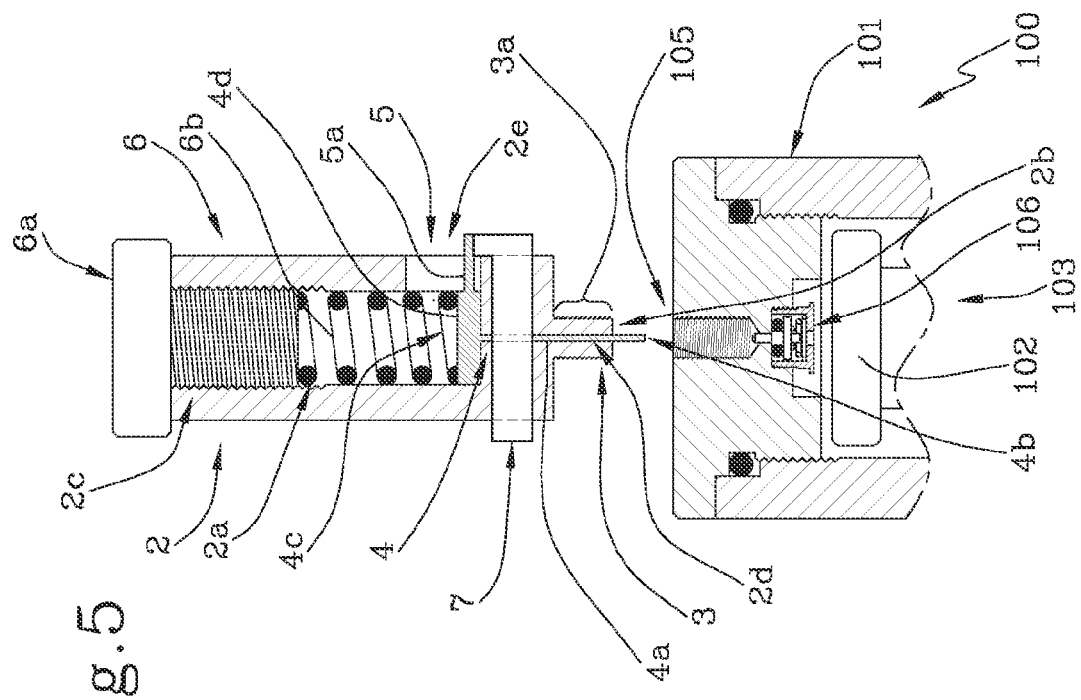
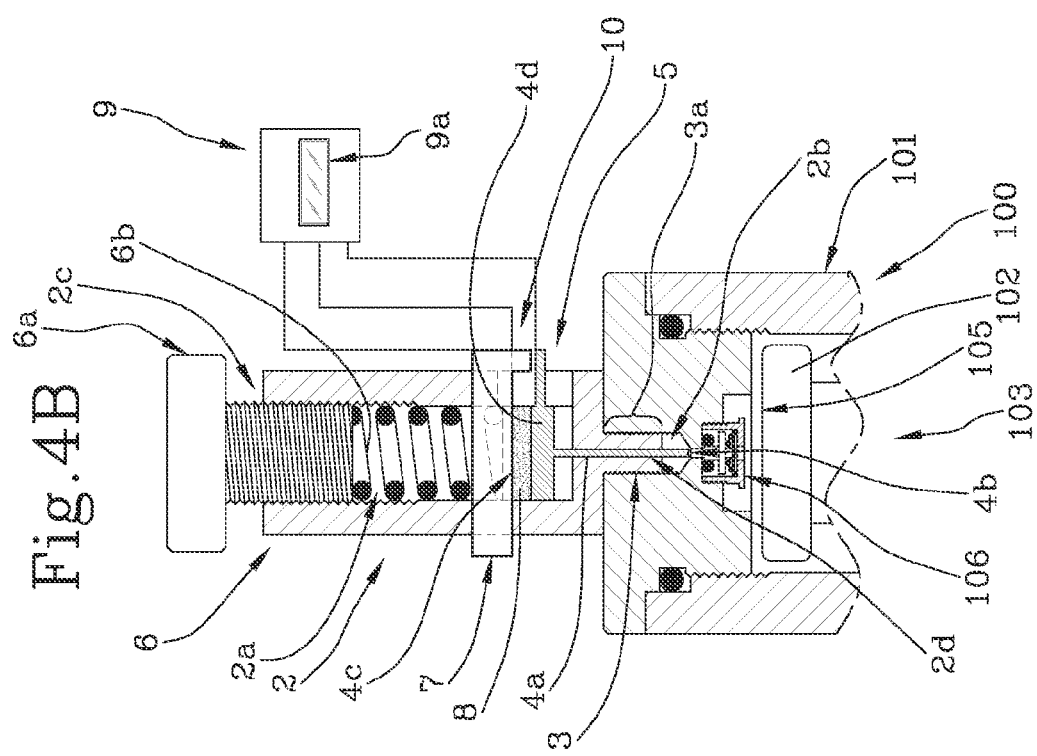

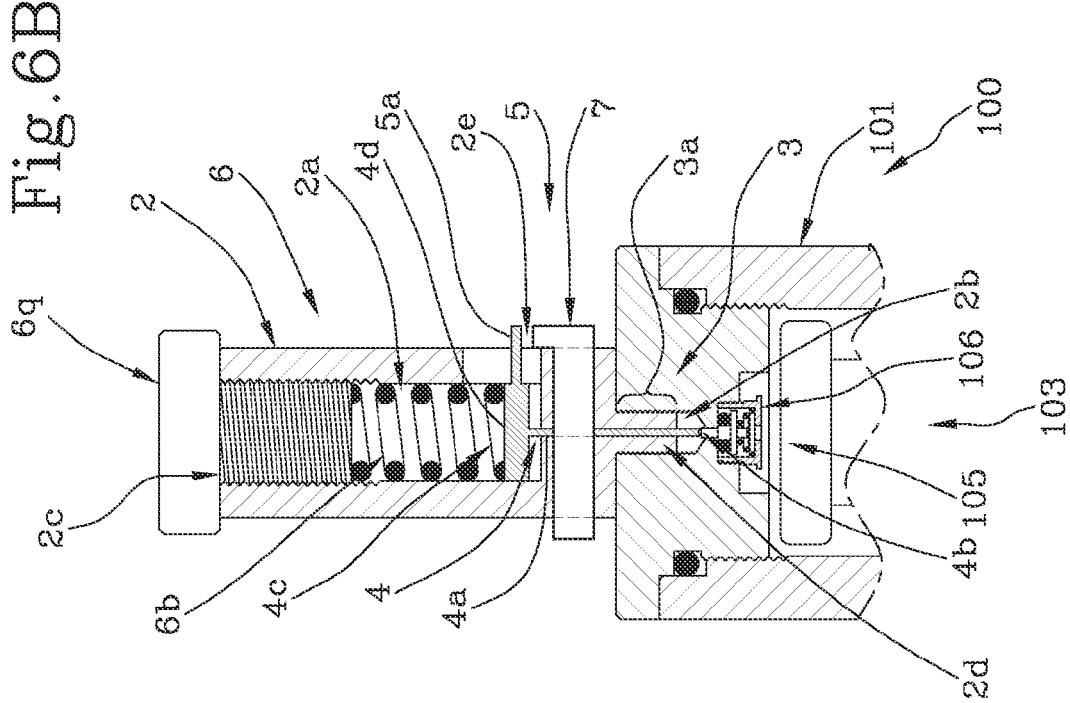
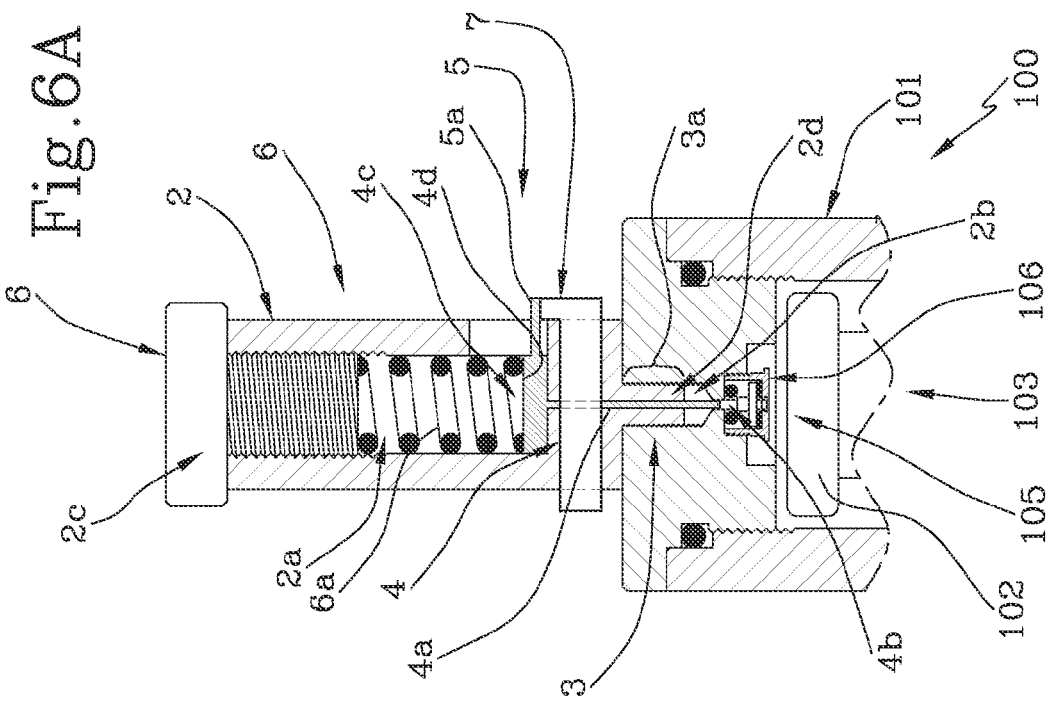

DEVICE AND METHOD FOR CHECKING THE STATE OF CHARGE OF A GAS SPRING

FIELD OF THE INVENTION

This invention relates to a device and a method for checking the state of charge of a gas spring.

More specifically, this invention relates to a device and a method for checking the state of charge of gas springs used in the suspension systems of male and/or female dies, especially in the context of pressing semi-finished metal parts.

DESCRIPTION OF RELATED ART

Generally speaking, during pressing, gas springs are known to be used to obtain the correct pressure between a male die and a female die and, if necessary, also their relative position, until the pressing has been completely formed.

The process of pressing a semi-finished part, also known as "pressing" in the jargon of the trade, involves cyclically moving a male die and a female die towards and away from each other in order to give relief and recessed shapes to a slab-shaped blank interposed between them, the male die and the female die being fixed to the ram (movable part) and bed of a press, respectively.

According to the above, the presence of gas springs at predetermined points of the die ensures that the stamping pressure at these points is the correct pressure needed to form the part correctly. Further, the use of gas springs to provide suspension for the male and female dies facilitates separation of the two parts of the die during the return stroke of the press ram.

In the context of this invention, the above mentioned gas springs, or alternatively, gas compression cylinders, are so called because they are usually charged with an inert gas, for example nitrogen.

The correct pressure of the gas inside the cylinder of the gas spring is fundamental for compression between the male die and the female to be identical and complete in each pressing cycle so that all the semi-finished parts made are identical in quality and dimensions.

In effect, if the pressure in the gas spring cylinder is too low, less force is applied by the compression system, in particular in the region of the die or forming structure where the gas spring is installed and interacts.

Since metal pressings are made in large quantities, the pressing process must be efficient and repeatable at all times. Thus, to guarantee optimum operating conditions of the gas springs used in the pressing process, periodic inspections are carried out, especially with regard to the state of charge of the gas springs, in order to detect possible gas leaks.

According to the state of the art, there are several different methods of checking the state of charge of gas springs, involving direct or calculated measurement of gas pressure inside the cylinder, or simply checking that the gas pressure does not deviate excessively from a predetermined nominal value for each specific cylinder model. More in detail, a first method entails checking the force applied by the gas spring by installing and compressing it in a laboratory dynamometer or in a press which is suitably equipped with a load cell capable of measuring the force. The measured value of the force provides an indirect indication of the state of charge, that is, the effective value of gas pressure in the gas spring, which must be equal to a nominal value.

A second, and more recent, method involves permanent installation—directly at a specific point in the gas spring cylinder—of an indicator of the state of pressurization in the cylinder.

Generally speaking, the indicator of the state of pressurization is installed at a bottom part of the gas spring cylinder, at a point different from the point where the charging valve of the gas spring is usually installed. To partly reduce the complexity of the machining work required for this solution, the seat for installing the charging valve and the seat for installing the indicator of the state of gas pressure are made at diametrically opposite positions on the cylinder, on the bottom cap of the cylinder, of the gas spring, for example by boring a single hole diametrically through the cylinder. This creates a thought duct by which the state indicator and the charging valve face each other. The system comprises a flexible element which is in contact with the pressure inside the cylinder. The flexible element adopts a deformed configuration in the presence of a nominal pressure level, stopping by interference an indicator which is visible to the user and slidable on guides. More specifically, the visible indicator adopts a predetermined position when the gas pressure is equal to the nominal value. If the pressure drops below the predetermined value, the flexible element tends to lose its deformed configuration, leaving the indicator at least partly free to slide on the guides. As it moves along the guides, the indicator uncovers a coloured region making its position, and hence the state of charge of the cylinder, even more evident.

All the methods known to the state of the art are subject to drawbacks and practical problems which make them difficult to implement in some cases.

More specifically, the first method, which involves checking the spring directly under a dynamometer or a test press, requires suitable instruments, as well as a dynamometer or press whose structure is suitable for the pressures to be measured and hence, for the forces developed by the gas springs. For example, a nominal gas spring charge of a few tons requires similar, if not higher, capacities of the measuring instruments and equipment. The costs of equipment of this kind are high and the first method is generally used when suitable testing machinery and equipment is already available. Moreover, in many cases, the passage from a pressure reading to a force value is not free of human errors and/or conversion errors.

The second method, that is, the indicator of the state of charge installed directly on the gas spring cylinder is also subject to some drawbacks. More specifically, making a seat especially for installing the indicator in the body of the cylinder is possible only when dimensions allow such a seat for the indicator to be machined in the cylinder. Up to the current state of the art, the machining work necessary for making the indicator seat in the cylinder is expensive and, moreover, constitutes an additional step in the production cycle. A further limitation of this solution is the added risk of gas leaks due to the additional hole in the cylinder of the spring, which might, over time, cause the performance of the gas spring to deteriorate.

Thus, the above mentioned solutions only partly solve the problem of providing a simple, accurate and immediate indication of the state of charge of a gas spring, especially for pressing processes.

SUMMARY OF THE INVENTION

In this context, the technical purpose of this invention is to provide a device for checking the state of charge of a gas spring to overcome the above mentioned disadvantages.

It is also an aim of this invention to provide a device for checking the state of charge of a gas spring and which offers greater flexibility of use than is normally known in the specific technical field, that is to say, whose use is possible for different gas spring models with pressure and performance properties which may differ considerably. Another aim of the invention is to provide a device for checking the state of charge of a gas spring and which is inexpensive, simple to use and free of all possible errors in the reading and/or interpretation of the response of the pressurized system being inspected.

A further aim of the invention is to provide a method for checking the state of charge of a gas spring and which is easy to implement and reliable.

These and other aims are substantially achieved by a device and a method for checking the state of charge of a gas spring, as described in one or more of the appended claims.

Further features and advantages of the present invention are more apparent from the detailed description of a preferred, but non-exclusive, embodiment of a device for checking the state of charge of a gas spring according to the invention.

BRIEF DESCRIPTION OF THE DRAWINGS

This description is made with reference to the accompanying drawings, which are also provided solely for purpose of non-limiting example and in which:

FIG. 2 is a sectional view of the device of FIG. 1 in a first step of a first form of use;

FIG. 3A is a sectional view of the device of FIG. 1 in a second step of a first form of use and in a situation where the gas spring is discharged;

FIG. 3B is a sectional view of the device of FIG. 1 in a second step of a first form of use and in a situation where the gas spring is charged;

FIG. 4A is a sectional view of the device in a first form of use and in an embodiment different from that shown in FIG. 1;

FIG. 4B is a sectional view of the device of FIG. 4A in a first form of use and in a situation where the gas spring is being checked;

FIG. 5 is a sectional view of the device of FIG. 1 in a first step of a second form of use;

FIG. 6A is a sectional view of the device of FIG. 1 in a second step of a second form of use and in a situation where the gas spring is discharged;

FIG. 6B is a sectional view of the device of FIG. 1 in a second step of a second form of use and in a situation where the gas spring is charged.

DETAILED DESCRIPTION OF PREFERRED EMBODIMENTS OF THE INVENTION

Figure 1:
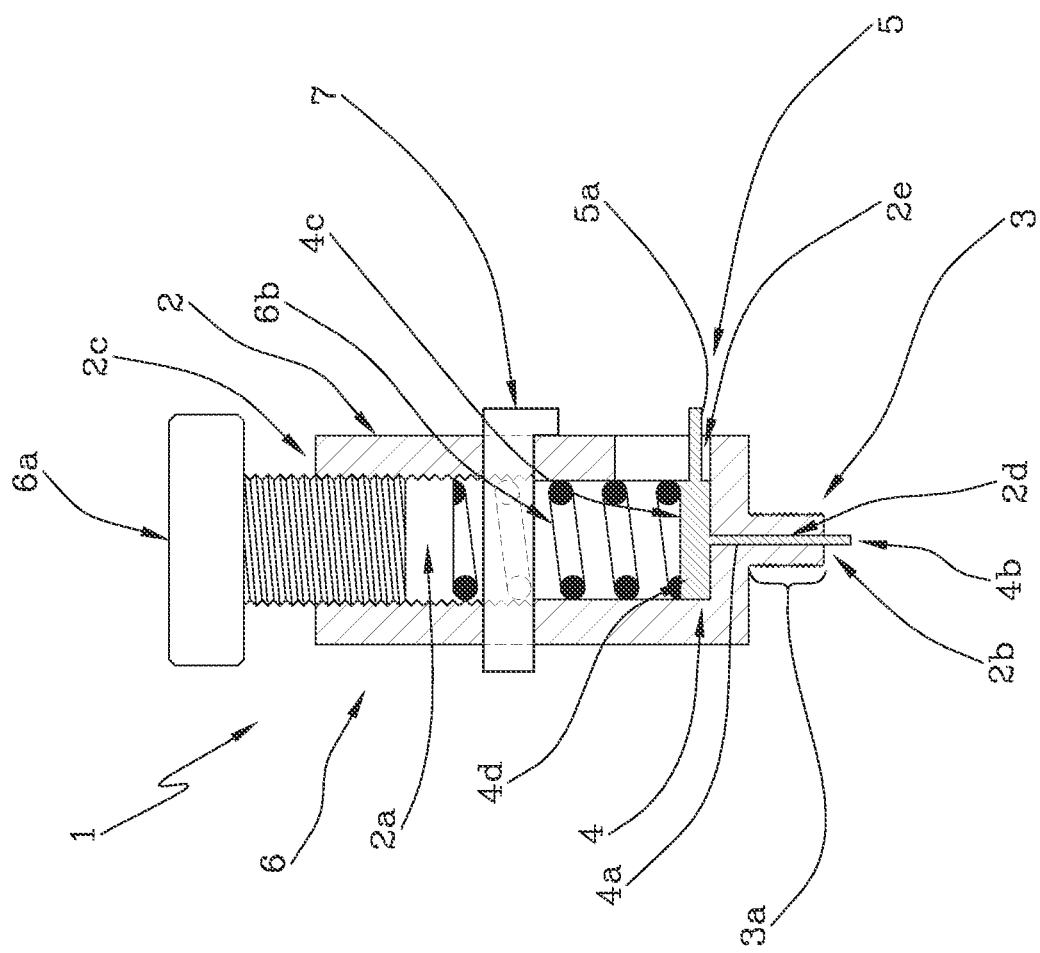
FIG. 1 is a sectional view of a device according to this invention.

FIG. 1 illustrates in its entirety a device for checking the state of charge of a gas spring according to this invention and in a preferred embodiment of the invention.

The checking device, denoted in its entirety by the reference numeral 1, comprises a container 2 having an internal cavity 2a and a termination 2b and, on the opposite side thereof, a hole 2c giving access to the internal cavity 2a.

Preferably, the container 2 of the checking device 1 is defined by a hollow cylindrical member having, on the side opposite to the access hole 2c, a protuberance whose transversal cross section is smaller than that of the container 2 and which defines the above mentioned termination 2b.

The termination 2b of the container 2 has a through hole 2d leading into the internal cavity 2a and thus in fluid communication with the selfsame internal cavity 2a.

The checking device 1 comprises a plunger 4 slidably housed in the through hole 2d. Preferably, the portion of the plunger 4 which is housed and slidable in the through hole 2d is defined by a rod 4a of the plunger 4.

The rod 4a of the plunger 4 has a first end 4b adapted to protrude from the through hole 2d of the termination 2b (on the side opposite to the internal cavity 2a) and a second end 4c which is slidably inserted in the internal cavity 2a of the container 2 and which has an abutment surface 4d.

Preferably, the abutment surface 4d of the plunger 4 defines a widening in the cross section compared to the rod 4a.

The checking device 1 comprises a position indicator 5 applied to the plunger 4 and such as to be externally visible to a user, in particular visible from the outside of the container 2 of the device 1.

In order to be effectively visible from the outside, the position indicator 5 comprises, in a preferred embodiment shown in the accompanying drawings, a protrusion 5a applied transversely to the plunger 4 (to the rod 4a or the abutment surface 4d) and inserted in a lateral opening 2e in the container 2, so that the protrusion 5a protrudes visibly from the container 2 and, if necessary, is accessible to the touch. Preferably, the protrusion 5a projects to a certain extent relative to the outside surface of the container 2 through the aforementioned lateral opening 2e which may, for example, have the shape of a slot or other suitable shape. Advantageously, this makes the protrusion 5a visible from different angles other than directly facing the lateral opening 2e, for example from lateral angles at 90° or more to the direction of extension of the protrusion 5a.

In this situation, the internal cavity 2a is in communication with the atmosphere, thus exposing the plunger 4, and in particular the abutment surface 4d, to atmospheric pressure.

In a possible variant embodiment, not illustrated in the accompanying drawings, the position of the plunger 4 is visible through a lateral opening 2e which has a transparent cover. This transparent cover, which is fixed directly to the container 2, has the effect of isolating the internal cavity 2a from the outside atmosphere, thus allowing the possibility of a pressure difference between the internal cavity 2a and atmospheric pressure.

The checking device 1 also comprises pushing means 6 designed to interact with the plunger 4 of the device 1, in particular with the abutment surface 4d, to apply thereon a predetermined thrust as necessary when the checking device 1 is being used.

In a preferred embodiment, the pushing means 6 comprise a screw element 6a which is rotatably engaged in the access hole 2c, that is to say, is screwed into it. That way, at least one portion of the screw element 6a screwed into the access hole 2c is located inside the internal cavity 2a and faces the abutment surface 4d of the plunger 4. In this situation, the screw element 6a defines a cap which closes the access hole 2c and whose position (along the internal cavity 2a) is adjustable by varying the screwing configuration of the screw element 6a in the access hole 2c.

The pushing means 6 also comprise an elastic element 6b interposed between the screw element 6a and the abutment surface 4d, in such a way that screwing in the screw element 6a causes compression of the elastic element 6b which is opposed by the selfsame abutment surface 4d of the plunger 4. In other terms, the compression applied by the pushing means 6 produces a force, or rather a thrust, on the plunger 4. The thrust on the plunger 4 is therefore adjustable by varying the screwing configuration of the screw element 6a in the access hole 2c which results in a variation of the axial position of the front end of the screw element 6a, facing the abutment surface 4a.

The aforementioned pushing means 6 are capable of applying a measured thrust on the plunger 4, in particular by adjusting the screwing configuration of the screw element 6a in the access hole 2c which produces measured compression of the elastic element 6b.

In short, by measured thrust is meant a thrust whose value is known to the user: the term "measured thrust" is explained in more depth below.

Preferably, the elastic element 6b of the pushing means 6 comprises a helical spring adapted to be housed in the internal cavity 2a of the container 2.

The checking device 1 according to the invention may also comprise a reference element 7 applied to the outside of the container 2 to define a locating reference for identifying the position adopted by the position indicator 5, in particular by the protrusion 5a projecting outwards from the container 2.

It should be noted that the reference element 7 must be considered as optional and designed to facilitate identification of the position adopted by the position indicator 5 and hence by the plunger 4 during an operating condition of use of the checking device 1.

The reference element 7 is particularly effective when the lateral opening 2e is not directly visible to the user, for example when the user looks at the container 2 from an angle substantially perpendicular to the direction of extension of the position indicator 5. In effect, to define a positional reference to assess the displacement, if any, of the position indicator 5, only the perimeter walls of the lateral opening 2e of the container 2 may be necessary, for example. The reference element 7 has the shape of a ring or ring nut, preferably axisymmetric so as to provide a reference for a user observing it from a wide range of angles.

The reference element 7 also comprises means, not illustrated in the accompanying drawings, for fastening it to the outside of the container 2 of the checking device 1. By way of example, the aforementioned means may be: grub screws, bolts, pins, threaded bosses and the like.

FIGS. 2 and 3A-3B show a sequence of operating steps for checking a gas spring 100 using the checking device 1 described above.

More specifically, the checking device 1 is applied stably, and reversibly, to the gas spring 100 by inserting the aforementioned termination 2b into a corresponding socket 105 formed on the gas spring 100.

For this purpose, the termination 2b is provided with connecting means 3 for stable, and reversible, connection to the receiving seat 105 of the gas spring 100.

The connecting means 3 preferably comprise an external thread 3a designed to engage an internal thread formed on the receiving seat 105 of the gas spring 100. In a variant embodiment not illustrated, the connecting means 3 comprise a pair of jaws designed to securely grip the outer covering of the gas spring.

The connecting means 3 on the termination 2b might also be embodied in any other way suitable for guaranteeing a secure hold (for example, bayonet or other connections).

In accordance with the technical context of this invention, the gas spring 100 is described as an element including a cylinder 101 and a piston 102 slidably coupled to each other and defining, in conjunction with each other, an internal space 103 containing a gas under pressure.

Preferably, the receiving seat 105 is formed on the cylinder 101 at a bottom wall of the cylinder 101, that is to say, at a position opposite the piston 102.

In detail, the cylinder 101 of the gas spring 100 has a charging valve 106 preferably located in a bottom portion of the seat 105. In general terms, the charging valve of a gas spring is a normally closed valve. This arrangement of the charging valve 106 is such that in the configuration where the checking device 1 is coupled to the gas spring 100, as shown in FIGS. 2, 3A-3B, 4A-4B, 5, 6A-6B, the first end 4b of the plunger 4 (opposite to the abutment surface 4d) is in contact with a movable sealing element of the charging valve 106. This contact may cause the charging valve 106 to open when the pressure of the gas in the internal space 103 of the cylinder 101, is less than a predetermined nominal pressure and, more specifically, is not high enough to overcome the action of the pushing means 6.

Advantageously, the predetermined nominal pressure corresponds exactly to the aforementioned measured thrust, whose value is known to the user and which is set on the checking device 1 in such a way that the user can directly interpret the response of the pressurized gas spring system (that is, the assembly made up of cylinder 101, internal space 103, gas and piston 102) based on a sliding movement of the plunger 4 caused by the pushing means 6.

In other terms, the user of the checking device 1 may set the value of the measured thrust applied by the pushing means 6 (by turning the screw element 6a as required) in such a way that the measured thrust value corresponds to a nominal pressure value of the gas spring 100 to be checked. That way, if the pressure of the gas in the gas spring 100 is less than the nominal value, the pushing means 6 cause the charging valve 106 of the gas spring 100 to open, thereby discharging the gas therein contained. In this situation, the plunger 4 reaches a position of maximum extension (outermost position) outside the through hole 2d, that is to say, towards the charging valve 106.

Where the pressure of the gas inside the gas spring 100 is greater than or equal to the aforementioned nominal value, on the other hand, the pushing means 6 are unable to overcome the force of the gas pressure and the charging valve 106 does not change over to the open position. In this situation, the plunger 4 adopts a retracted position inside the through hole 2d.

Thus, by observing the position adopted by the position indicator 5, the user can see whether the gas pressure in the gas spring 100 is too low (position indicator 5 in extended position) or optimal (position indicator 5 in retracted position).

Described below with reference in particular to FIGS. 2 and 3A, 3B is a first form of use of the checking device 1.

According to this first form of use, the corresponding checking method comprises the following steps:
  preparing a gas spring 100 (for example of the type described above);
  preparing a checking device 1 like the one described above;
  securely connecting the gas spring 100 to the checking device 1 by inserting the termination 2b of the checking device 1 into the receiving seat 105 of the gas spring 100;
  following activation of the pushing means 6, observing whether the position indicator 5 is displaced or not, indicating whether or not there is a difference between the pressure of the gas in the gas spring 100 and a nominal value.

In the first form of use, activation of the pushing means 6 occurs after securely connecting the checking device 1 to the gas spring 100. By so doing, the plunger 4, under the action of the pushing means 6, comes into abutment with the charging valve 106 of the gas spring 100 only after they have been coupled to each other. Thus, preparing the checking device 1 before connecting it to the gas spring 100 occurs when the screw element 6a of the checking device 1 is in the rest configuration, that is to say, in the configuration where it does not compress the elastic element 6b or compresses it to a level below operating level.

Further, the pushing means 6 are activated manually by the user by turning the screw element 6a and thus causing the elastic element 6b to be compressed to apply force to the plunger 4. More specifically, screwing in the screw element 6a increases the compression of the elastic element 6b.

As an effective aid to the user and a precise system for easily resetting the same compression condition, the screw element 6a may have, for example, a graduated scale ranging from a minimum pressure value to a maximum pressure value (not illustrated in the accompanying drawings) to be set against a fixed reference mark on the container 2: each mark on the scale corresponds to a value of the force applied to the plunger 4 and hence of the pressure applied by the same on the charging valve 106. Generally speaking, this relation is true when the elastic property (denoted by "k" in technical jargon) of the elastic element 6b is also known.

Advantageously, the aforementioned measured thrust value applied by the pushing means 6 can be set by the user, preferably continuously, according to a plurality of values ranging from a minimum value to a maximum value.

For example, the minimum measured thrust value of the checking device 1 is zero when the screw element 6a is disengaged from the elastic element 6b (elastic element 6b discharged). On the other hand, the measured thrust value of the checking device 1 is at its maximum when it is such that it overcomes the pressure of the gas inside the internal space 103 and is preferably less than or equal to a nominal value of 500 bar.

Thus, if the pressure of the gas inside the internal space 103 of the gas spring 100 is less than the nominal value (spring discharged), the plunger 4 causes the charging valve 106 to open and the rod 4a is accordingly pushed out of the termination 2b, as shown in FIG. 3A. If the pressure of the gas is greater than or equal to the nominal value, on the other hand (optimum spring charge condition), the plunger 4 does not change position and the valve 106 remains closed, as shown in FIG. 3b.

The use of the reference element 7 may help the user to see whether the plunger 4 has moved or not, according to one of the two conditions of use of the first embodiment of the checking device 1.

More in detail, according to the method of the invention— in a situation where the checking device 1 is securely connected to the gas spring 100 but the pushing means 6 have not been activated yet (the plunger 4 is at the most retracted position)—the reference element 7 can be adjusted in such a way as to abut against the position indicator 5 (also at its most retracted position) in contact with the charging valve 106 and locked at that position on the outside of the container 2, for example with a threaded boss.

Next, the user activates the pushing means 6 as described above and checks whether the position indicator 5 moves relative to the reference element 7, indicating that the plunger 4 has moved and hence that the pressure of the gas in the gas spring 100 is too low.

FIGS. 4A and 4B illustrate a first form of use of the checking device 1 in a different embodiment thereof.

With reference to FIGS. 4A and 4B, the checking device 1 comprises an electronic sensor 8, preferably interposed between the abutment surface 4d of the plunger 4 and the end of the elastic element 6b facing the abutment surface 4d.

The sensor 8 converts into an electrical signal the force and/or pressure applied between the abutment surface 4d and the aforestated end of the elastic element 6b.

By way of an example, the sensor 8 is a pressure sensor or a load cell. Preferably, the sensor 8 has a shape and/or size which make it suitable for being housed inside the internal cavity 2a of the checking device 1, without producing interference and friction, especially when the pushing means 6 are actuated, with the walls of the internal cavity 2a of the container 2.

The checking device 1 also comprises an electronic instrument 9 for processing and displaying the electric signal generated by the sensor 8.

Preferably, the electronic instrument 9 displays on a display unit 9a the physical quantity associated with the electric signal generated by the sensor 8. Preferably, the electronic instrument 9 is powered by an external electrical network.

Preferably, the sensor 8 is connected to the electronic instrument 9 by electric wiring, as also illustrated in FIGS. 4A, 4B.

A mechanical microswitch 10, or more generally, an ON-OFF contact, is located between the position indicator 5 of the plunger 4 and the reference element 7. Preferably, the mechanical microswitch 10 is housed outside the container 2.

The state of the mechanical microswitch 10 is normally open, that is to say, its contact is normally not closed and, therefore, no signal is transmitted by the sensor 8 to the electronic instrument 9.

The mechanical microswitch 10 switches from an open state to a closed state when the reference element 7 comes into abutment against the position indicator 5.

More in detail, according to the method of the invention, in a situation where the checking device 1 is securely connected to the gas spring 100, the electronic instrument 9 is connected to an external electrical power network and is on. At this stage, the pushing means 6 are not yet activated (the plunger 4 is at its most retracted position) and the mechanical microswitch 10 is normally open.

Next, the reference element 7 is adjusted by the user in such a way that it abuts the position indicator 5 (also at its most retracted position) in contact with the charging valve 106 and locked in place on the outside of the container 2.

Abutment between the position indicator 5 and the reference element 7 interacts with the contact of the mechanical microswitch 10, allowing it to change over to the closed state, so that the electric signal generated by the sensor 8 is enabled to reach the electronic instrument 9, which is already powered up and switched on (FIG. 4A).

At this stage, the electronic instrument 9 emits a visual or other form of state signal (for example, the display unit 9a flashes) to tell the user that the sensor 8 is in operation and properly generating a signal interpreted by the selfsame electronic instrument 9.

Next, the user activates the pushing means 6 as described above, until the display unit 9a of the electronic instrument 9 changes state.

As soon as the measured thrust of the checking device 1 is such as to overcome the pressure of the gas inside the gas spring 100, the position indicator 5 simultaneously moves relative to the reference element 7, indicating the movement of the plunger 4 such as to open the charging valve 106 of the gas spring 100.

The movement, that is, the lack of contact, between the position indicator 5 and the reference element 7 causes the mechanical microswitch 10 to change back to an open state.

The changeover of the mechanical microswitch 10 back to its prior state allows the last signal sent by the sensor 8 to the electronic instrument 9 and stored therein to be processed by the electronic instrument 9 and to be displayed on the display unit 9a in terms of a physical quantity, for example, force. The electronic instrument 9 preferably also emits an acoustic signal to alert the user.

Upon being alerted, the user stops activating the pushing means 6 (FIG. 4B).

Once the value of the force which has caused the charging valve 106 of the gas spring 100 to open is known, as shown on the display unit 9a, the user can find the value of the pressure inside the gas spring 100 by using ready conversion tables, divided according to the different models of the gas springs 100, or using a single conversion formula.

The checking device 1 may also comprise a more advanced electronic instrument 9, provided, for example, with a more complete user interface.

The advanced electronic instrument 9 allows storing in an electronic memory the technical specifications of all the available models of the gas springs 100, so that the user can—each time the gas spring 100 is checked—call up the specific model of the gas spring 100 in order to view immediately on the display unit 9a the value of the pressure inside the gas spring 100 and, consequently, also the value of the force generated thereby.

FIGS. 5, 6A and 6B illustrate a second form of use of the checking device 1.

According to this second form of use, the corresponding checking method comprises the following steps:
- preparing a gas spring 100 as described above;
- preparing the checking device 1 as described above, where the pushing means 6 have already been activated;
- securely connecting the gas spring 100 to the checking device 1 by inserting the termination 2b of the checking device 1 into the receiving seat 105 of the gas spring 100;
- observing whether the position indicator 5 is displaced or not, indicating whether or not there is a difference between the pressure of the gas in the gas spring 100 and a nominal value.

In a first embodiment, the pushing means 6 are activated at the factory during assembly of the checking device 1. In other terms, the checking device 1 is preferably sold with the pushing means 6 already activated (preloaded) and set for a predetermined type of gas spring 100. This may be achieved either by using the checking device 1 with the structure described above, where the screw element 6a is already tightened in a predetermined configuration, or by using a different structure for the checking device 1, for example with a generic cap stably fixed, for example by welding or other fastening systems, and hence factory set according to a predetermined thrust value which cannot be modified by the user.

Alternatively to what is described above, in the second form of use, the pushing means 6 might be activated beforehand by the user just before applying the checking device 1 to the gas spring 100, for example manually by fully tightening the screw element 6a according to the steps of the method described above and according to a predetermined nominal value, or by tightening the screw element 6a up to a desired level lower than the maximum value (for example, when checking a plurality of gas springs 100 with different specifications).

In a preferred embodiment, the embodiment with the factory-set pushing means 6 comprises pre-loading the pushing means 6 on the plunger 4 to a level slightly lower than the nominal thrust operating on the charging valve 106 of the gas spring 100 under optimum conditions (gas spring charged).

More in detail, in a situation where the checking device 1 has pre-activated pushing means 6, the reference element 7 is fixed to the outside of the container 2 in a position such as to abut against the position indicator 5 at its most extended position and to allow the position indicator 5 to be retracted (as illustrated in FIGS. 5, 6A and 6B), thus offering a solution which is the opposite of that described above with reference to the first form of use of the checking device 1. Next, the user securely connects the checking device 1 to the gas spring 100, as described above, and checks whether the position indicator 5 moves relative to the reference element 7.

For example, the minimum value of measured thrust (measured preloading) of the checking device 1 is such as to overcome a gas pressure inside the internal space 103 less than or equal to a nominal value of 10 bar, while the maximum value of measured thrust (measured preloading) of the checking device 1 is such as to overcome a gas pressure inside the internal space 103 less than or equal to a nominal value of 500 bar.

More specifically, the aforementioned measured thrust value (measured preloading) can be set, preferably continuously, according to a plurality of values ranging from the minimum value to the maximum value mentioned above.

In short, and in more general terms, the method for checking the state of charge of a gas spring according to the invention, comprises the following steps:
- preparing a gas spring in such a way as to make it accessible to a charging valve for the same;
- preparing a plunger element configured to apply a force on the gas spring charging valve;
- applying a force on the charging valve through the agency of the plunger;
- measuring the intensity of the force applied by the plunger on the charging valve;
- holding the gas spring locked firmly in position during the step of applying a force on the charging valve;
- detecting the extent of a displacement of the plunger relative to a reference element.

More specifically, the step of measuring the intensity of the force comprises the sub-step of associating the plunger element to force measuring means, preferably to a dynamometer. Alternatively, and more preferably, the step of measuring the intensity of the force comprises the sub-step of connecting the plunger element to an elastic element having a predetermined preloading such as to apply a known, preset load on the plunger. Still more preferably, the step of measuring the intensity of the force comprises the sub-step of continuously setting the value of the force according to a plurality of values ranging from a minimum value to a maximum value.

The method according to the invention also comprises the step of associating a position indicator with the plunger element.

Advantageously, the checking device 1 according to the invention is suitable for checking the state of charge of a gas spring 100 mounted in any position: horizontal, vertical or any other intermediate position, even upside down.

Advantageously, the checking device 1 according to the invention is not invasive and does not produce gas leaks each time the state of charge of an optimally charged gas spring 100 is checked. In effect, being optimally charged, the pressure of the gas inside these springs is high enough to prevent the charging valve 106 from being opened by the plunger 4 of the checking device 1. Where the pressure of the gas in the gas spring 100 is too low, on the other had, gas flowing out as a result of the opening of the charging valve 106 must not be considered as a disadvantage because in such a case, the gas spring would already be in a condition unsuitable for use and thus scheduled for recharging or disposal.

In this regard, an important advantage offered by the invention is that of being able, by adjusting the pushing means 6, to set the thrust value which allows distinguishing between gas springs 100 in a condition suitable for use (the plunger 4 of the checking device 1 is unable to open the charging valve 106 of the gas spring 100) and gas springs 100 in a condition unsuitable for use (the plunger 4 of the checking device 1 opens the charging valve 106 of the gas spring 100). It is therefore sufficient to set the pushing means 6 by fixing a predetermined thrust value below which the gas spring 100 must be considered no longer usable.

The above also improves the flexibility of use of the checking device, making it suitable for application to a wide range of gas springs 100, requiring only that the pushing means 6 be preloaded to a value predetermined as required according to the type of gas spring 100 to be checked.

Moreover, should it be necessary to completely discharge the internal space 103 of the gas spring 100 (prior to recharging or disposal of a discharged gas spring 100) the checking device 1 also allows the gas to be discharged directly into the outside atmosphere so that the gas spring 100 can be scheduled for disposal or recharging.

Whatever the case, even if the opening of the charging valve 106 of the gas spring 100 by the checking device 1 must not allow gas to escape to the outside, all that needs to be done is to provide the connecting means 3 with an elastic O-ring seal.

Advantageously, the checking device 1 allows the state of charge of a gas spring 100 to be checked without using a press or a dynamometer or other specific instruments or equipment. This aspect allows considerable savings in terms of time, needed for checking the gas spring 100, and costs of the instruments (press, dynamometer, load cell or pressure gauge), suitable for checking according to the prior art.

Furthermore, since the checking device 1 allows precise measurement and selection of the pressure value to be checked, there is no risk of misinterpretation and/or errors converting the measured value of pressure and/or thrust.

Advantageously, the device 1 is made from simple components which are quick and easy to make using traditional machine tools.

Advantageously, the device 1—thanks to its constructional simplicity—is guaranteed for long-life operation without necessitating maintenance, retuning or calibration, as is, instead, often the case with many measuring instruments. Advantageously, the elastic element 6b inside the device 1 is an interchangeable component which is readily available on the market as a standard mechanical component listed according to size and elastic property (denoted by the letter "k" in technical jargon).

When necessary, the user can advantageously substitute the elastic element 6b (when the pushing means 6 are removable), thus resetting the device 1 with another value of measured thrust, and hence of pressure to be checked in a different set of gas springs 100.

The invention claimed is:

1. A device (1) for checking the state of charge of a gas spring (100), comprising:
   a supporting structure (2) equipped with connecting means (3) adapted to be reversibly connected to a gas spring (100);
   a plunger (4) slidably received, at least partly, in the supporting structure and having a first end (4b) adapted to interact, in conditions of use, with a charging valve of a gas spring, the plunger having a second end which has an abutment surface (4d);
   pushing means (6) operating on the abutment surface (4d) of the plunger (4) to apply a measured thrust on the plunger (4) such as to induce the displacement thereof;
   a position indicator (5) operatively associated with the plunger (4) and configured to represent the position of the plunger relative to a reference element (7).

2. The device (1) according to claim 1, wherein the pushing means (6) comprise a screw element (6a) which is rotatably engaged on the supporting structure (2) and an elastic element (6b) which is interposed between the screw element (6a) and the abutment surface (4d) of the plunger (4) in such a way that a predetermined degree which the screw element (6a) is screwed to corresponds to a predetermined degree of compression of the elastic element (6b), so that the elastic element (6b) applies a predetermined compressive force on the plunger (4).

3. The device (1) according to claim 1, wherein the position indicator (5) comprises a protrusion (5a) applied transversely to the plunger (4) and inserted in a lateral opening (2e) of the supporting structure (2) so that the protrusion (5a) protrudes visibly outwards from the supporting structure (2).

4. The device (1) according to claim 1, wherein the reference element (7) is applied to the outside of the supporting structure (2) to define a locating reference for identifying the position adopted by the position indicator (5).

5. The device (1) according to claim 1, comprising a sensor (8), preferably a transducer for converting force and/or pressure into an electrical signal representing the intensity of the force and/or pressure, interposed between the abutment surface (4d) of the plunger (4) and the elastic element (6b) in order to measure a value of the compression which screwing the screw element (6a) causes to be applied on the elastic element (6b).

6. The device (1) according to claim 5, further comprising:
   a display unit for making available to a user the electric signal detected by the sensor (8) and representing the intensity of the force and/or pressure;
   a memory unit for storing at least the last electric signal measured by the sensor (8) and sending it, on a user's request, to the display unit.

7. The device (1) according to claim 1, wherein the connecting means (3) comprise an external thread (3a) formed on a termination (2b) of the supporting structure (2).

8. The device (1) according to claim 1, wherein the connecting means (3) comprise a pair of jaws.

9. A method for checking the state of charge of a gas spring 100), comprising the following steps:
   preparing a gas spring (100) in such a way as to make it accessible to a charging valve for the same;
   preparing a plunger element configured to apply a force on the gas spring charging valve;
   applying a force on the charging valve through the agency of the plunger;
   measuring the intensity of the force applied by the plunger on the charging valve;
   holding the gas spring locked firmly in position during the step of applying a force on the charging valve;
   detecting the extent of a displacement of the plunger relative to a reference element.

10. The method according to claim 9, wherein the step of measuring the intensity of the force comprises the sub-step of associating the plunger element to force measuring means, preferably to a dynamometer.

11. The method according to claim 9, wherein the step of measuring the intensity of the force comprises the sub-step of connecting the plunger element to an elastic element having a predetermined preloading and such as to apply a known, preset load on the plunger.

12. The method according to claim 9, further comprising the step of associating a position indicator to the plunger element.

13. The method according to claim 9, wherein the step of measuring the intensity of the force comprises the sub-step of continuously setting the value of the force according to a plurality of values ranging from a minimum value to a maximum value.

\* \* \* \* \*